United States Patent
Franco et al.

(10) Patent No.: US 12,348,948 B2
(45) Date of Patent: Jul. 1, 2025

(54) GENERATING TORSO SHAPES SUITABLE FOR SYNTHESIS OF HEAD-RELATED TRANSFER FUNCTIONS

(71) Applicant: HARMAN INTERNATIONAL INDUSTRIES, INCORPORATED, Stamford, CT (US)

(72) Inventors: Alfredo Fernandez Franco, Sherman Oaks, CA (US); Christian Manuel Garcia, Winnetka, CA (US)

(73) Assignee: Harman International Industries, Incorporated, Stamford, CT (US)

( * ) Notice: Subject to any disclaimer, the term of this patent is extended or adjusted under 35 U.S.C. 154(b) by 287 days.

(21) Appl. No.: 18/186,823

(22) Filed: Mar. 20, 2023

(65) Prior Publication Data

US 2024/0323631 A1    Sep. 26, 2024

(51) Int. Cl.
| | |
|---|---|
| H04S 7/00 | (2006.01) |
| A61B 5/107 | (2006.01) |
| G06T 7/62 | (2017.01) |
| G06V 40/10 | (2022.01) |

(52) U.S. Cl.
CPC .............. *H04S 7/301* (2013.01); *A61B 5/107* (2013.01); *G06T 7/62* (2017.01); *G06V 40/103* (2022.01); *H04S 2420/01* (2013.01)

(58) Field of Classification Search
CPC ...... H04S 2420/01; H04S 7/301; H04S 7/302; H04S 2400/11; H04S 7/303; G06T 2207/20081; G06T 2207/30196; G06V 40/10

See application file for complete search history.

(56) References Cited

U.S. PATENT DOCUMENTS

2015/0312694 A1* 10/2015 Bilinski ................ H04S 7/301
                                                                 381/1

OTHER PUBLICATIONS

Hu et al., "Learning to Estimate the Body Shape Under Clothing From a Single 3-D Scan", IEEE Transactions on Industrial Informatics, DOI 10.1109/TII.2020.3016591, vol. 17, No. 6, Jun. 2021, pp. 3793-3802.

Dabral et al., "Learning 3D Human Pose from Structure and Motion", https:/ /doi.org/10.1007 /978-3-030-01240-3_41, Oct. 5, 2018, pp. 679-696.

Hasler et al., "Estimating Body Shape of Dressed Humans", Computers & Graphics, doi: 10.1016/j.cag.2009.03.026, vol. 33, No. 3, Jun. 2009, pp. 211-216.

(Continued)

*Primary Examiner* — Kile O Blair
(74) *Attorney, Agent, or Firm* — Artegis Law Group, LLP

(57) ABSTRACT

Disclosed embodiments include techniques for generating a clean 3D shape of a portion of the human torso of a subject from a 3D scan that includes overlaying surfaces that occlude a portion of the torso, where the overlaying surfaces are acoustically transparent, such as wrinkles on a t-shirt and/or other clothing surfaces. These techniques use heuristic constraints to generate a clean 3D shape of a human torso for the purpose of generating a more realistic head-related transfer function (HRTF) that is individualized for the subject. The improved HRTF, when applied to a sound system, leads to a more immersive and realistic acoustic experience for the subject when listening to music, experiencing a virtual reality experience, and/or the like.

20 Claims, 10 Drawing Sheets

(56) References Cited

OTHER PUBLICATIONS

Braren et al., "A High-Resolution Individual 3D Adult Head and Torso Model for HRTF Simulation and Validation: 3D Data", DOI: 10.18154/ RWTH-2020-06760, 2020, pp. 1-4.
Gordon et al., "Anthropometric Survey of U.S. Army Personnel: Summary Statistics, Interim Report for 1988", Mar. 1, 1989, https://apps.dtic.mil/sti/citations/ADA209600, 335 pages.

* cited by examiner

GENERATING TORSO SHAPES SUITABLE FOR SYNTHESIS OF HEAD-RELATED TRANSFER FUNCTIONS

BACKGROUND

Field of the Embodiments of the Present Disclosure

Embodiments of the present disclosure relate generally to three-dimensional (3D) modeling systems and, more specifically, to techniques for generating torso shapes suitable for synthesis of head-related transfer functions.

DESCRIPTION OF THE RELATED ART

Audio systems often employ various techniques to improve audio quality and realism experienced by listeners, also referred to herein as subjects, of these audio systems. One such technique is an anatomically-based technique that measures how audio waves reach the human ear. Such techniques involve computing head-related transfer functions (HRTFs) that characterize how sound is transformed by the human torso. In particular, the shape and size of the torso, head, ears, ear canals, oral cavities, nasal cavities, and/or the like can cause amplification of sound and/or attenuation of sound at certain frequencies. By computing the HRTF of a subject, an audio source can take this amplification of sound and/or attenuation into account when generating sound, thereby improving the audio experience of the subject. HRTFs can be particularly effective in specific applications, such as generating binaural audio, dynamically rendering virtual audio sources, and/or the like.

In some cases, HRTFs can be measured on a variety of human subjects and/or human mannequins, and averaged to generate a generic HRTF that can be employed for any subject. While using such generic HRTFs to render binaural audio can improve audio quality for the average subject, these generic HRTFs do not take into account the physical characteristics of a particular subject. Therefore, audio quality can be improved by computing an individualized HRTF that is customized for each particular subject. An individualized HRTF for a subject can be measured directly on the subject in-situ. In-situ measurements of HRTFs typically require specialized equipment and acoustic environment. Therefore, in-situ measurements of HRTFs are impractical for a large number of subjects, such as for consumer products with a large user base.

Alternatively, an individualized HRTF for a subject can be measured by generating a 3D scanned model of the subject and synthesizing the HRTF using this 3D model. A 3D scan of a subject can be measured and, together with acoustical numerical methods, the HRTFs can be synthesized. The 3D scan can also be used to generate a torso simulator that can be used to measure the HRTF for that subject.

One potential drawback with the above approach is that 3D scans of human torsos can include surfaces that are not acoustically relevant. For example, when generating a 3D scan of a human torso, the subject's clothing can appear as a solid surface. For example, the wrinkles on a t-shirt and/or other clothing are acoustically transparent, and therefore should not affect the HRTF. However, because the 3D scan of wrinkles on clothing appears as a solid surface, the resulting HRTF is affected by the solid surfaces that represent clothing. As a result, the 3D scan of a subject with clothing can result in significant distortion of the HRTF synthesis. Although this effect can be somewhat mitigated if the subject wears no clothing during the 3D scan, this may not be practical under certain circumstances. Another approach for mitigating the effects of this distortion is for a digital artist to manually remove the surfaces corresponding to the subject's clothing. However, this manual process can be painstaking, prone to error, and can require someone with special skills to perform.

As the foregoing illustrates, improved techniques for generating 3D models used in synthesis of head-related transfer functions would be useful.

SUMMARY

Various embodiments of the present disclosure set forth a computer-implemented method for generating torso shapes suitable for synthesis of head-related transfer functions. The method includes inputting a three-dimensional (3D) scan into a machine learning model, wherein the 3D scan depicts one or more surfaces overlaying a human body structure comprising a torso of a user, wherein the one or more surfaces occlude a portion of the torso. The method further includes generating, via execution of the machine learning model, a clean shape representing a shape of the torso including the portion occluded by the one or more surfaces, wherein the machine learning model is trained on one or more target shapes using a loss function based on at least one heuristic constraint that specifies a constraint value that constrains a property of a first target shape of the one or more target shapes, wherein the heuristic constraint is derived from a database of anatomical relationships. The method further includes causing the clean shape to be outputted in a computing device, wherein the clean shape is suitable for generating an accurate head-related transfer function for the user.

Other embodiments include, without limitation, a system that implements one or more aspects of the disclosed techniques, and one or more computer readable media including instructions for performing one or more aspects of the disclosed techniques.

At least one technical advantage of the disclosed techniques relative to the prior art is that 3D torso models for synthesizing head-related transfer functions can be generated faster and more accurately than with prior conventional approaches. In particular, the 3D torso models generated with the disclosed techniques do not include surfaces that are not acoustically relevant for HRTF purposes, such as wrinkles on a t-shirt and/or other clothing surfaces. As a result, these 3D torso models can be used to synthesize and generate individualized HRTF without the need for manual processes to remove acoustically transparent surfaces from the 3D torso models. Further, manual processes can introduce errors, asymmetry, and inaccuracy in the resulting 3D model. By contrast, 3D torso models generated with the disclosed techniques are more accurate and consistent with the shape of the torso of the subject being scanned. As a result, synthesized HRTF data derived from these 3D torso models are likewise more accurate and suitable for the subject being scanned. These technical advantages represent one or more technological improvements over prior art approaches.

BRIEF DESCRIPTION OF THE SEVERAL VIEWS OF THE DRAWINGS

So that the manner in which the recited features of the one or more embodiments set forth above can be understood in detail, a more particular description of the one or more embodiments, briefly summarized above, may be had by reference to certain specific embodiments, some of which are illustrated in the appended drawings. It is to be noted, however, that the appended drawings illustrate only typical embodiments and are therefore not to be considered limiting of its scope in any manner, for the scope of the disclosure subsumes other embodiments as well.

DETAILED DESCRIPTION

In the following description, numerous specific details are set forth to provide a more thorough understanding of certain specific embodiments. However, it will be apparent to one of skill in the art that other embodiments may be practiced without one or more of these specific details or with additional specific details.

Various disclosed techniques include a computer-based system that employs a machine-learning model that predicts correct 3D torso shapes given a distorted 3D scan of a human torso. The system corrects the distorted 3D scan and generates an improved 3D model of the torso. The improved 3D model of the torso generated by the machine-learning model can be used for synthesis of HRTFs through acoustic simulations, or through the generation of physical 3D models of the scanned subject.

The machine-learning model is generated by training a machine learning/artificial (ML/AI) model with a target dataset that includes scanned 3D imagery of human torsos. The scanned 3D imagery is obtained using a device that captures high resolution 3D models of a human subject. The device can be, a computerized tomography (CT) imager, a light detection and ranging (lidar) scanner, a photogrammetry device, a camera device, and/or the like. In some examples, the skin depth of the subject is visible in the scanned 3D imagery. The target dataset is processed using heuristics that indicate a desired acoustic performance when synthesizing HRTFs based on the 3D models that are processed to include an anatomically correct torso. These heuristics include body volume, shape consistency, proportions, joint locations, symmetry, and/or the like. The desired acoustic performance is defined as the difference between the synthesized HRTF and the measured HRTF for each subject in the target dataset. This difference can be quantified as a difference in acoustical pressure or as a psychoacoustic performance in terms of sound quality or localization accuracy.

The target dataset is then used to generate a machine-learning model that describes the transformation applied to a new scan of a subject as captured by a computing system fitted with sensors and/or scanning devices. The machine-learning model processes the new scan to generate a processed model that is optimized for HRTF synthesis.

Figure 1:
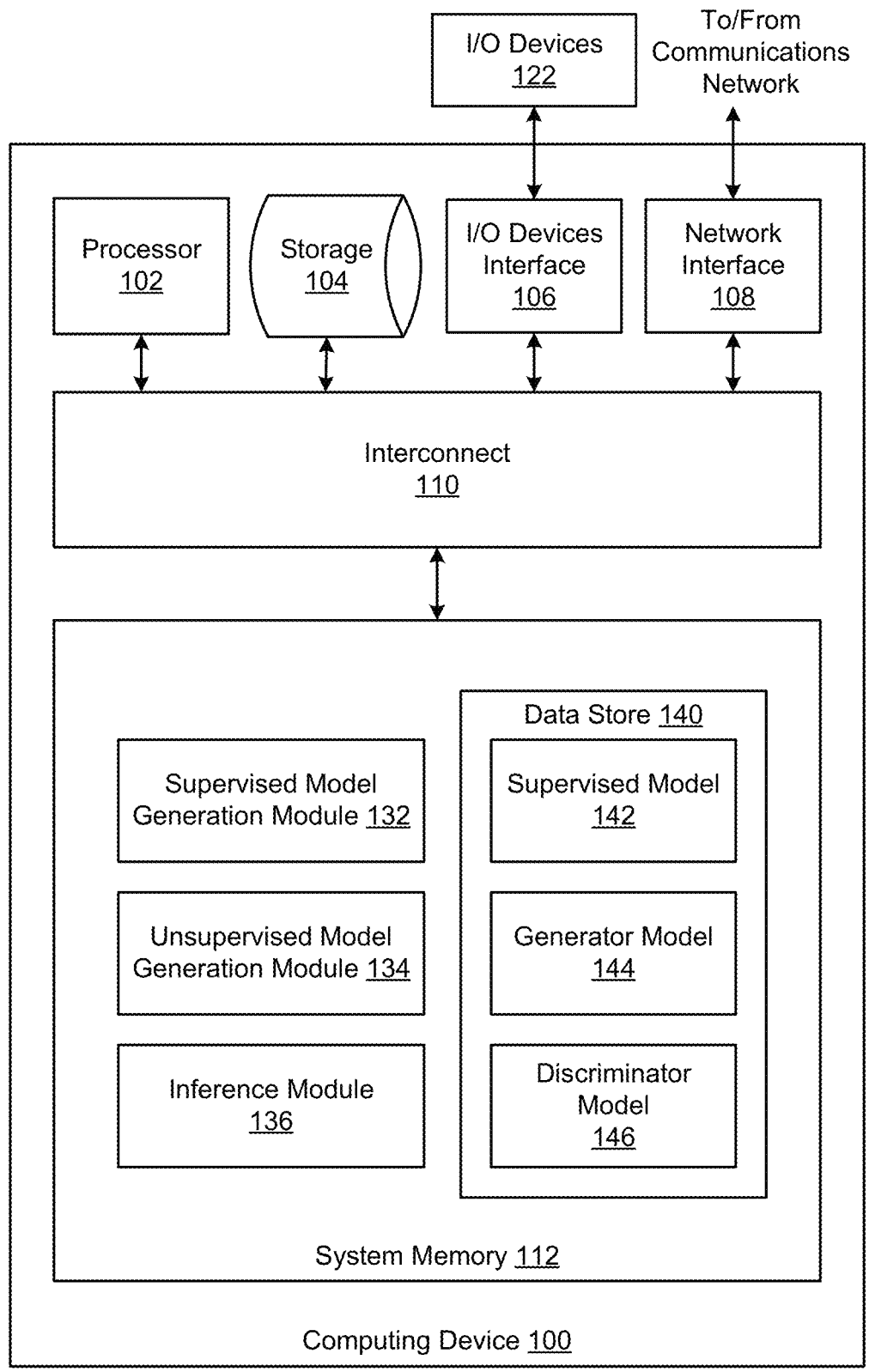
FIG. 1 illustrates a computing system configured to implement one or more aspects of the various embodiments.

FIG. 1 illustrates a computing device 100 configured to implement one or more aspects of the various embodiments. As shown, the computing device 100 includes, without limitation, a processor 102, storage 104, an input/output (I/O) devices interface 106, a network interface 108, an interconnect 110, and a system memory 112.

The processor 102 retrieves and executes programming instructions stored in the system memory 112. Similarly, the processor 102 stores and retrieves application data residing in the system memory 112. The interconnect 110 facilitates transmission, such as of programming instructions and application data, between the processor 102, I/O devices interface 106, storage 104, network interface 108, and system memory 112. The I/O devices interface 106 is configured to receive input data from user I/O devices 122. Examples of user I/O devices 122 may include one or more buttons, a keyboard, a mouse or other pointing device, and/or the like. The I/O devices interface 106 may also include an audio output unit configured to generate an electrical audio output signal, and user I/O devices 122 may further include a speaker configured to generate an acoustic output in response to the electrical audio output signal. Another example of a user I/O device 122 is a display device that generally represents any technically feasible means for generating an image for display. For example, the display device could be a liquid crystal display (LCD) display, organic light-emitting diode (OLED) display, or digital light processing (DLP) display. The display device may be a TV that includes a broadcast or cable tuner for receiving digital or analog television signals. The display device may be included in a head-mounted display (HMD) assembly such as a VR/AR headset or a heads-up display (HUD) assembly. Further, the display device may project an image onto one or more surfaces, such as walls, projection screens or a windshield of a vehicle. Additionally or alternatively, the display device may project an image directly onto the eyes of a user (e.g., via retinal projection).

The processor 102 is included to be representative of a single central processing unit (CPU), multiple CPUs, a single CPU having multiple processing cores, digital signal processors (DSPs), field-programmable gate arrays (FPGAs), graphics processing units (GPUs), tensor processing units, and/or the like. And the system memory 112 is generally included to be representative of a random-access memory. The storage 104 may be a disk drive storage device. Although shown as a single unit, the storage 104 may be a combination of fixed and/or removable storage devices, such as fixed disc drives, floppy disc drives, tape drives, removable memory cards, or optical storage, network attached storage (NAS), or a storage area-network (SAN). The processor 102 communicates to other computing devices and systems via the network interface 108, where the network interface 108 is configured to transmit and receive data via a communications network.

The system memory 112 includes, without limitation, a supervised model generation module 132, an unsupervised model generation module 134, an inference module 136, and a data store 140. The data store 140 includes, without limitation, a supervised model 142, a generator model 144, and a discriminator model 146. The supervised model generation module 132, unsupervised model generation module 134, and inference module 136, when executed by the processor 102, perform one or more operations associated with the techniques described herein.

The supervised model generation module 132 generates the supervised model 142 using supervised learning. The unsupervised model generation module 134 generates the generator model 144 and the discriminator model 146 using unsupervised learning. In some embodiments, the supervised model generation module 132 and supervised model 142 are optional. After training of the generator model 144 is complete, an inference module 136 uses one or more components of the trained generator model 144 to generate one or more clean shapes 306. The inference module 136 provides a 3D scan and an optional input vector as input to the generator model 144 and receives clean shapes 306 from the generator model 144. The inference module 136 then provides the clean shapes 306 to other system components such as application program code or the like.

When performing operations associated with the supervised model generation module 132, the processor 102 stores data in and retrieves data from portions of the data store 140, such as the supervised model 142. When performing operations associated with the unsupervised model generation module 134, the processor 102 stores data in and retrieves data from portions of the data store 140, such as the generator model 144 and the discriminator model 146. When performing operations associated with the inference module 136, the processor 102 stores data in and retrieves data from portions of the data store 140, such as the generator model 144.

Figure 2:
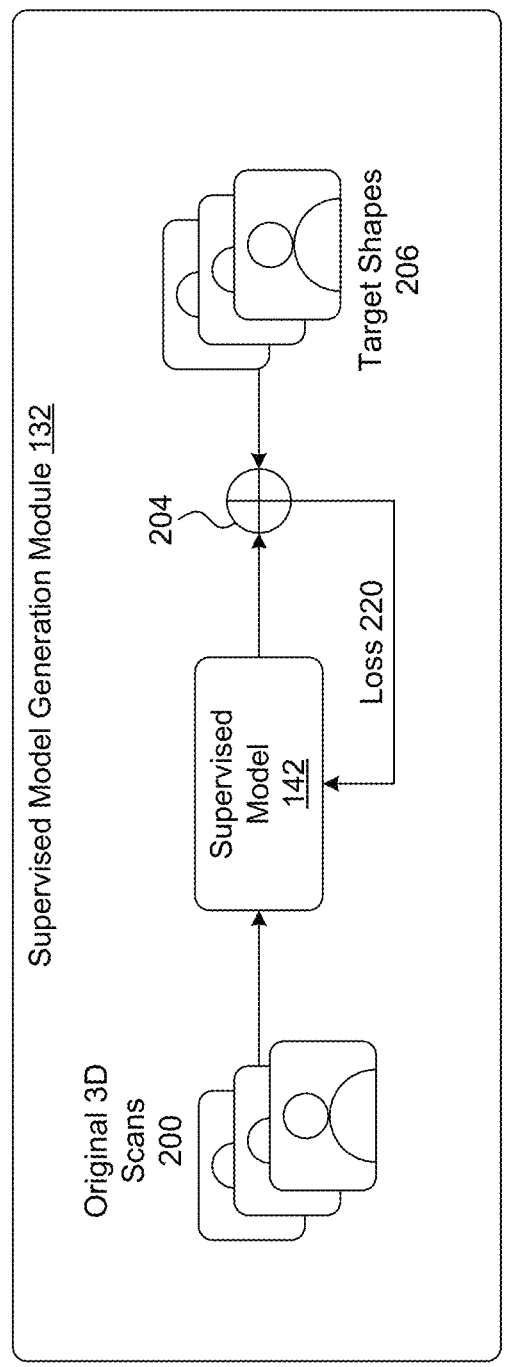
FIG. 2 is a block diagram of the supervised model generation module of FIG. 1, according to various embodiments.

FIG. 2 is a block diagram of the supervised model generation module 132 of FIG. 1, according to various embodiments. The supervised model generation module 132 trains a supervised model 142 using tagged training data to transform a 3D optical scan of an at least partially covered human body structure that includes additional surfaces, such as clothes or hair that cover at least a portion of the body structure, to a "clean" shape of the body structure without the additional surfaces. As described above, the accuracy of an HRTF for a particular person is dependent on the shape of at least a portion of the body structure of the person. The terms "clean shape" and "body structure" as used herein refer to the shape delineated by the contours of a person's skin. The term "occluded shape" as used herein refers to a shape having at least one surface that optically occludes at least a portion of an underlying human body structure. A body structure may be optically occluded in the scan by one or more covering objects such as clothing or hair. As a result of the occlusion by the covering objects, the optical scan does not accurately depict the underlying shape of the human body structure in the areas that are optically occluded. The covering objects are substantially acoustically transparent, and so do not substantially occlude sound waves. An HRTF generated from the shape depicted in the 3D scan is thus based on an inaccurate depiction of the acoustically significant shape of the torso. Such a distorted HRTF is likely to produce audibly distorted results if used in practice. One approach to generating a clean shape from a 3D scan of an occluded shape involves training a supervised machine learning model 142, using supervised training, to output a clean shape that approximates the body structure of a person depicted in a given 3D scan. Supervised training uses training data in which example input data is tagged, e.g., labeled, with corresponding examples of output data. The tagged training data includes original 3D scans 200 and corresponding target shapes 206. The original 3D scans 200 may be example scanned shapes of at least partially occluded human body structures that include additional surfaces such as clothes or hair, and the target shapes 206 may be example shapes of the respective human body structures that do not include the additional surfaces. The supervised model generation module 132 trains the supervised model 142 using a loss function 204 that determines an amount of loss between a clean shape (not shown) output by the supervised model 142 and a target shape 206. Each 3D scan and shape may be represented as a point cloud. The loss function 204 can compute a difference between the clean shape and the target shape based on Euclidean distances between points on the clean shape and points on the target shape when the centers of mass of the clean shape and target shape are aligned, for example. The supervised model generation module 132 trains the supervised model 142 using backpropagation of the loss 220 to the supervised model 142. During training, each iteration of a training process causes the supervised model 142 to generate an example clean shape based on one of the original 3D scan 200, computes an amount of loss based on a difference between the generated clean shape and a target shape 206 that corresponds to the original 3D scan 200, and updates parameters (e.g., weights) of the supervised model 142 to reduce the amount of loss. As a result of the training process, the supervised model 142 can map 3D scans of occluded underlying human body structures to clean shapes that approximate the underlying human body structures.

Figure 3:
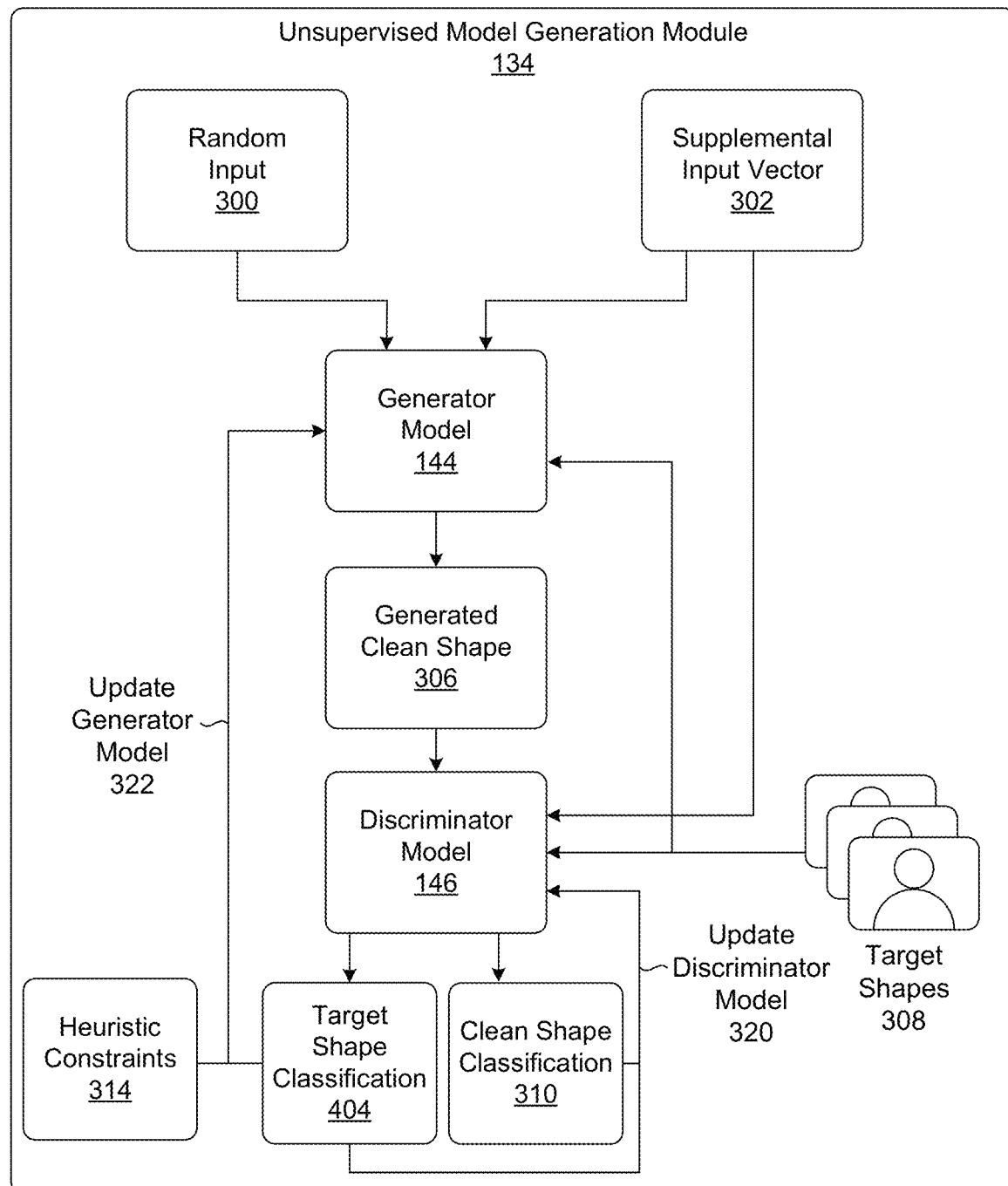
FIG. 3 is a block diagram of the unsupervised model generation module of FIG. 1, according to various embodiments.

FIG. 3 is a block diagram of the unsupervised model generation module 134 of FIG. 1, according to various embodiments. The unsupervised model generation module 134 trains a generative adversarial network (GAN) using unsupervised learning. The GAN incudes a generator model 144 and a discriminator model 146. In unsupervised learning, at least a portion of the training process is performed using untagged training data. The untagged training data may include example target shapes 308 representing clean shapes of human body structures, which are the desired output of the unsupervised model. However, the training data does not include example input data corresponding to the example target shapes 308, as would be available in supervised learning. Instead, the unsupervised learning process trains the generator model 144 to generate clean shapes 306 of human body structures by transforming random input 300 into clean shapes 306 that are similar to the example target shapes 308 and conform to heuristic constraints 314. The example target shapes 308 can be, for example, a set of training images depicting naked torsos.

The unsupervised learning process may also use a form of training data referred to herein as a "supplemental input vector" 302, which can include one or more tags representing anatomical characteristics such as height, body mass index, and the like. The tags may be provided with the target shapes used for training, or may be determined from the target shapes during the training process. Anatomical characteristics specified by the tags can be used as a supplemental input vector 302 to direct the clean shape generation process of the unsupervised machine learning model at inference time if desired anatomical characteristics of the clean shapes are provided as input to the generator model 144. The desired anatomical characteristics may be characteristics of the person for whom the clean shape is being generated. For example, a user may provide their height and body mass index for use as a supplemental input vector 302 to the generator model 144 at inference time. The generator then generates a clean shape having the specified height and body mass index.

The unsupervised training is performed using a GAN training process, which trains the generator model 144 and the discriminator model 146 in respective separate phases. The GAN training process alternates between the discriminator training phase and the generator training phase until a termination condition is met. The GAN includes a generator model 144, which generates a clean shape 306 based on random input 300 and a supplemental input vector 302, as described above. The generated clean shape 306 can be represented as a convex hull constructed from a set of points in 3D space.

The GAN uses the discriminator model 146 to distinguish between target shapes 308, which are referred to herein as "real" shapes, and generated clean shapes 306, which are referred to herein as "fake" shapes. The discriminator model 146 generates a clean shape classification 310 for each clean shape 306. The classification 310 classifies the clean shape 306 as being either "real" (e.g., similar to target shapes 308) or "fake" (e.g., not similar to target shapes 308). The discriminator model 146 also generates a classification of each target shape 308. The target shape 308 may be from a training dataset, for example. The discriminator's classification of the clean shape 306 is referred to as an amount of "fake loss," and the discriminator's classification of the target shape 308 is referred to as an amount of "real loss." A discriminator loss function determines a total amount of discriminator loss by combining (e.g., adding) the fake loss and the real loss. The unsupervised model generation module 134 performs a discriminator model update operation 320, which involves backpropagation to train the discriminator model based on the amount of discriminator loss. The backpropagation updates parameters (e.g., weights) of a neural network in the generator to reduce the amount discriminator loss.

The unsupervised model generation module 134 also trains a generator model 144 to generate clean shapes 306. The unsupervised model generation module 134 invokes a generator loss function, which determines an amount of generator loss based on a sum of the fake loss and an amount of heuristic loss determined by a body heuristic loss function (not shown). The fake loss is referred to as "adversarial loss" in the generator training process. The heuristic loss represents a difference between the clean shape 306 and shapes described in a database of anatomical relationships. For example, the heuristic loss may be a difference between a torso height of the clean shape 306 and an average torso shape height specified in the database. performs a generator model update operation 322, which updates parameters of the generator model 144 based on a sum of the adversarial loss and the heuristic loss as determined by a generator loss function.

Figure 4:
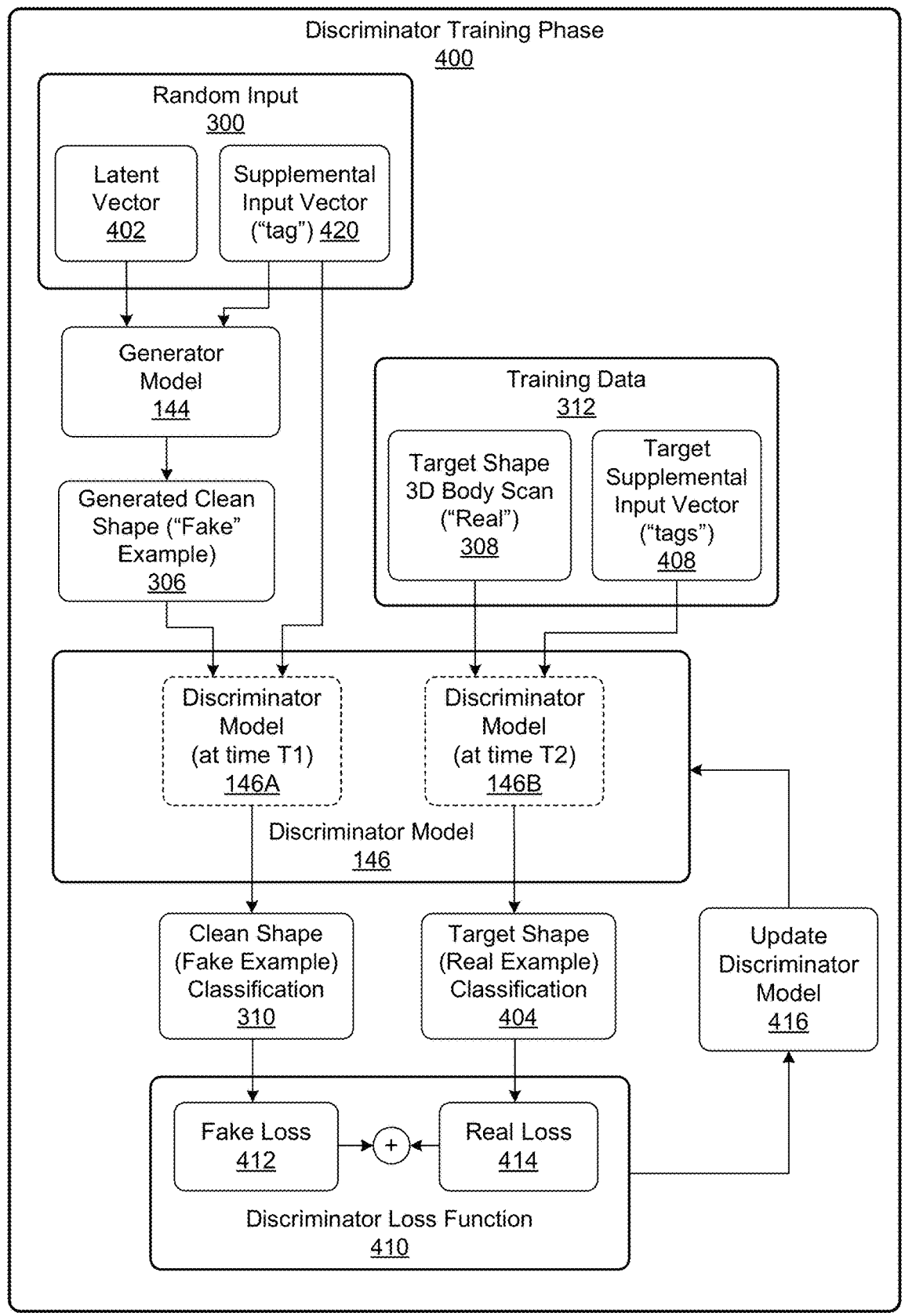
FIG. 4 is a more detailed view of how the discriminator model of FIG. 3 is trained, according to various embodiments.
Figure 5:
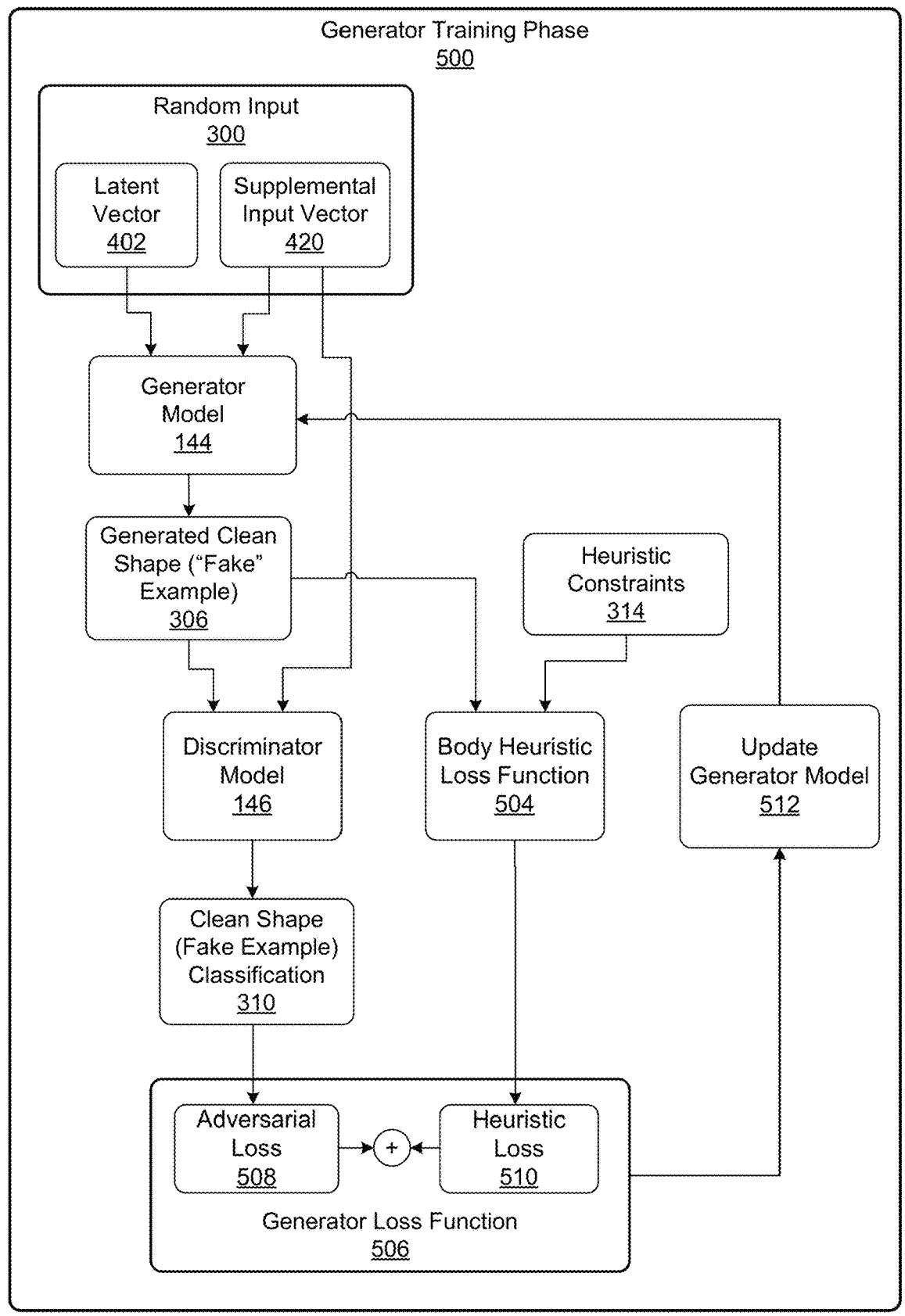
FIG. 5 is a more detailed view of how the generator model of FIG. 3 is trained, according to various embodiments.

FIG. 4 is a more detailed view of how the discriminator model 146 of FIG. 3 is trained, according to various embodiments. The unsupervised learning techniques disclosed herein involve training a GAN. The GAN training process trains a discriminator model 146 and a generator model 144. As described above, the training process alternates between a discriminator training phase 400 and a generator training phase 500. For clarity, the discriminator training phase 400 and the generator training phase 500 are shown separately, although in practice the training phases are performed on the same GAN, alternating between the two phases until a threshold condition is met. The GAN components involved in the discriminator training phase 400 are illustrated in FIG. 4, and the GAN components shown in the generator training phase 500 are illustrated in FIG. 5. The discriminator training phase 400 uses training data 312 that includes target shapes 308 and target supplemental input vectors 408. The target shapes 308 represent clean human body structures. Each target shape 308 can be represented as a convex hull generated based on a set of points in 3D space, for example. Training the GAN results in a trained generator model 144 ("generator") that can be used to generate clean shapes 306 resembling the target shapes 308 and conforming to one or more heuristic constraints 314.

A shape can have one or more properties, and each property can have an associated value. For example, a height property of a shape can have a value of 5 feet, 7 inches. Other example properties include a waist circumference, a ratio of shoulder width to torso height, a body mass index, and so on. A heuristic constraint 314 can specify that a designated property value of the shape is equal to a specified constraint value. The constraint value can be a specific value, e.g., 5 feet, 7 inches for the height property. As an example, a constraint criterion can specify that the constrained property is a height of a shape, and that the constraint value is 5 feet, 2 inches. A constraint can be specified in a loss function, for example. A loss function can calculate the difference between a shape property value identified by a constraint and a constraint value specified by the constraint. Constraint values can be derived from a database of anatomical relationships, or other suitable data source.

By adding a heuristic constraint term to a loss function used to train a generator model, a GAN network can be trained to generate torsos having properties that approximate or are equal to constraint values specified by the constraints. For example, by adding a height constraint specifying an average height to the loss function, the GAN can be trained to generate torsos having heights close to or the same as the average height from the database of anatomical relationships. Using this term causes the GAN to generate shapes having torsos that are representative of the size and shape of the population represented in the database.

Additionally, the training data 312 may include target supplemental input vectors 408 on which the trained generator model 144 is further conditioned. A supplemental input vector 408 can include one or more elements, which are referred to herein as "tags." The supplemental input vector 408 can include specific values or ranges for body characteristics such as body mass index, shoulder circumference, chest circumference, and so on. When the trained generator model 144 is used to generate a clean shape 306 for a particular person, one or more tags can be provided as input to the generator model 144 at inference time to cause the generator model 144 to generate clean shapes 306 that were associated with the tag(s) when the generator model 144 was trained (e.g., the specified tags were included in the training data. At inference time, each generated clean shape 306 has one or more characteristics specified by the tag(s) in the target supplemental input vector 408 associated with at least one of the target shapes from which the clean shape 306 is generated. The target shapes from which the clean shape 306 is generated are selected by the generator model 144, e.g., because of similarity to a 3D scan 602 provided to the generator model 144 at inference time. Further, the clean shape 306 can also be generated by the generator model 144 based on other factors, such as heuristic constraints 314, described below with respect to FIG. 5, and/or the supplemental input vector ("tags") 604 described below with respect to FIG. 6. Thus, the clean shape 306 can have one or more property values that approximate or are the same as respective heuristic constraint values associated with the heuristic constraints 314. Further, the clean shape 306 can have characteristics associated with the supplemental input vector ("tags") 604, e.g., a particular height or a height in a particular range specified by the supplemental input vector 604.

In some examples, a user of a mobile device can create a clean shape 306 based on a scan of a portion of their body, such as a torso, using of an application executing on the mobile device. The application can use the camera and/or other imaging device of the mobile device to capture a 3D scan of the portion of the user's body and request one or more optional tags from the user. The user can provide a tag that corresponds to the user's height, e.g., 5 feet and 7 inches. The application then provides the 3D scan and the tag to a generator model, which generates a clean shape 306 of a torso resembling the torso depicted in the 3D scan for a body of the user-specified height.

In the unsupervised training process for the GAN, the generator model 144 ("generator") is trained to generate a clean shape 306, e.g., a 3D object, that conforms to a set of heuristics constraints. The heuristic constraints can be from a database of anatomical relationships, such as average height, average waist circumference, average shoulder circumference, and so on.

The generator model 144 can be executed by an execution engine that receives inputs for the generator model 144, provides the inputs to the generator model 144, and provides outputs of the generator model 144 to other system components. Upon execution, the generator model 144 generates clean shapes 306 that are similar to target shapes 308 on which the generator was trained, and that conform to the anatomical relationships specified by the heuristic constraints. As described herein, the generator model 144 is trained on training data 312, which includes target shapes 308 representing specific body portions, such as a torso without additional surfaces. Further, the target shapes 308 that are used to train the generator model 144 satisfy heuristic constraints representing particular anatomical relationships. The clean shape 306 output by the generator model 144 conforms to the heuristic constraints, so the clean shape 306 has the properties specified by the heuristic constraints. Thus, the heuristic constraints are used to guide the unsupervised training process to produce a generator model 144 that generates clean shapes 306 having the properties specified by the heuristic constraints.

Figure 6:
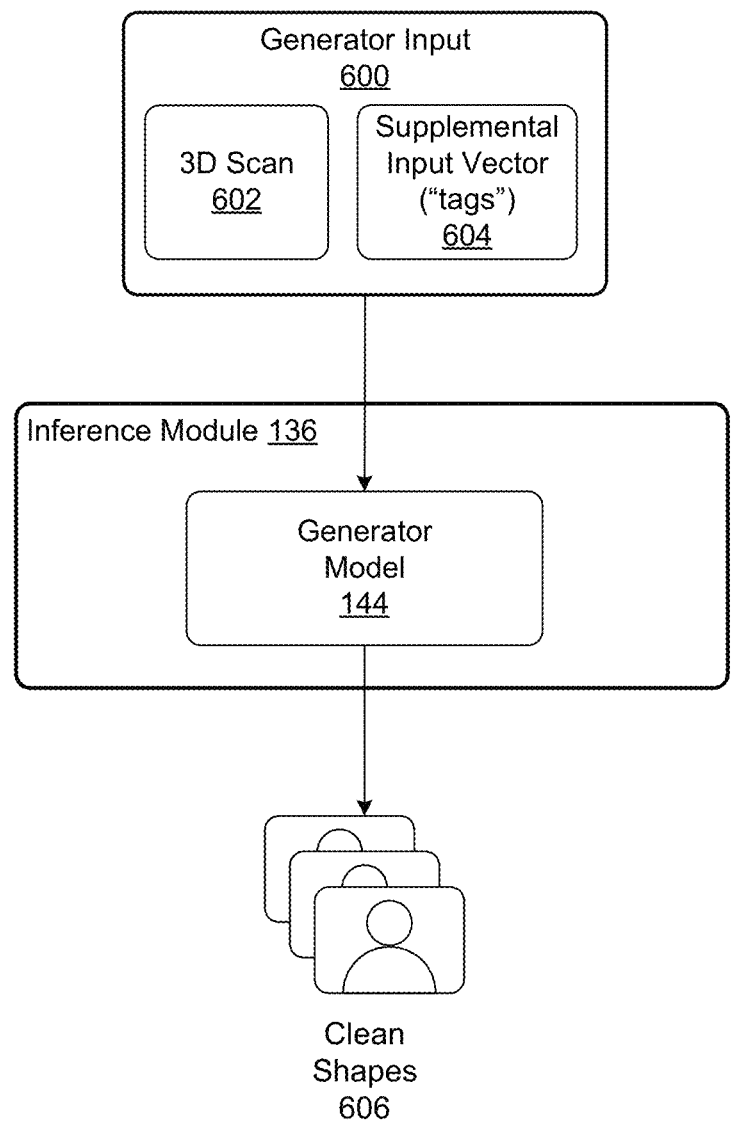
FIG. 6 is a block diagram of the inference module of FIG. 1, according to various embodiments.

Additionally, as described herein with respect to FIG. 6, input can be provided to the trained generator model 144 specifying further properties of the clean shapes 306 to be generated. The input can include a 3D scan 602 of a human body structure that includes additional surfaces that are not integral parts of the body structure, such as clothes or hair. Providing the 3D scan of a particular human body structure, such as that of a user, as input to the generator causes the generator to generate a clean shape that is similar in shape to the target images used to train the generator and conforms to the heuristics, while also having similarities to the input 3D scan.

Further, as described herein with respect to FIG. 6, the generator input 600 to the generator model 144 can include a supplemental input vector 604 ("tags") that specify body-related properties of the clean shape 306 to be generated. The supplemental input vector 604 can include specific values or ranges for body properties such as body mass index, shoulder circumference, chest circumference, and so on. The generator model 144 can be trained using particular values of the target supplemental input vector ("tags") 408 associated with the target shapes 308 in the training data 312. The target supplemental input vector 408 can be provided by the training data, e.g., determined by the provider of the training data. Alternatively or additionally, the target supplemental input vector 408 can be derived from the target shapes 308 prior to or during the training process. For example, if one of the tags in the target supplemental input vector 408 represents waist circumference, the training engine can identify a waist portion of a torso target shape 308 in the training data and calculate the circumference of the waist portion. The training engine can then use the calculated circumference as a tag associated with the torso target shape 308 and update the parameters of the generator model 144 as described herein. Each tag in a supplemental input vector 408 can include one or more values, which can be stored in a corresponding entry (e.g., element index) of an input vector for the generator. For example, a tag that represents a height may have the values 5 and 10 to represent 5 feet, 10 inches. As another example, a tag can represent a range of values, e.g., 130 pounds to 150 points for a weight range. A tag may represent a range of values so that a separate tag need not be used for each value in the range.

The training process for the GAN trains a discriminator model 146 and a generator model 144. The training process alternates between a discriminator training phase 400 and a generator training phase 500, which is described below with respect to FIG. 5. The discriminator model 146 is shown twice in FIG. 4 for clarity, as discriminator model 146A, which is used at a time T1, and discriminator model 146B, which is used at a different time T2. Discriminator model 146A, which represents discriminator model 146 at time T1, receives a generated clean shape 306 and an optional supplemental input vector 420 as input, and classifies received shape as being either "real" (e.g., from the training data 312) or "fake" (e.g., generated by the generator model 144). Discriminator model 146A generates a clean shape classification 310 as a value between 0 and 1.0, where 1.0 indicates that the clean shape 306 is classified as fake, 0 indicates that the clean shape 306 is classified as real, and a value between 0 and 1 indicates a probability that the clean shape 306 is fake. Discriminator model 146B, which represents discriminator model 146 at time T2, receives a target shape 308 and a target supplemental input vector 408 as input, and classifies the received shape as being either "real" (e.g., from the training data 312) or "fake" (e.g., generated by the generator model 144). Discriminator model 146B generates a target shape classification 404 as a value between 0 and 1.0, where 1.0 indicates that the target shape 308 is classified as real, 0 indicates that the target shape 308 is classified as fake, and a value between 0 and 1 indicates a probability that the target shape is real. Although particular probability values are described as corresponding to real and fake classification in the examples described herein, other probability values may correspond to the real and fake classifications in other examples.

The discriminator training phase 400 trains the discriminator using a discriminator loss function 410, which determines an amount of discriminator loss based on a sum of the two classifications 310, 404 output by the discriminator model. The discriminator training phase 400 updates parameters of the discriminator model 146 (e.g., neural network weights) by performing backpropagation (update discriminator model 416) based on the discriminator loss generated by the discriminator loss function 410.

The discriminator loss function 410 computes a discriminator loss based on a real loss 414 and a fake loss 412. The discriminator loss is a measure of how well the discriminator model 146 is able to distinguish between real and generated samples. The discriminator loss can be calculated as the sum of the log of the probability assigned by the discriminator to real examples being real and the log of the probability assigned to generated examples being fake. Taking the log of the probabilities enables the probabilities to be combined using addition. The discriminator loss function may calculate the real loss 414 as follows:

real_loss=−torso.log_prob(discriminator(torso))

where "torso" represents the target shape 308, and "discriminator" represents the discriminator model 146. Further, "log_prob" calculates the logarithm of a probability. The discriminator loss function can calculate the fake loss 412 as follows:

generated_torso=generator(torso)

fake_loss=generated_torso.log_prob(discriminator (generated_torso))

where "generator" represents the generator model 144 and "generated_torso" represents the clean shape 306. The discriminator loss function 410 can calculate the discriminator loss as a sum of the fake loss 412 and the real loss 414, and provide the discriminator loss to an update discriminator model 416 operation. The update discriminator model 416 operation can update the parameters (e.g., weights) of a neural network in the discriminator model 146 based on the discriminator loss, for example.

The training process alternates between the two phases 400, 500 until a threshold condition is met, such as the discriminator model 146 being unable to determine which of its inputs is real and which of its inputs is fake. For example, if the discriminator model 146 generates a clean shape classification 310 representing a probability of 0.5, then the training process stops because the discriminator model 146 is unable to distinguish between a target shape 308 and a clean shape 306 generated by the generator.

In the discriminator training phase 400, the training process provides random input 300 to the generator model 144 as input. The random input 300 includes a random latent vector 402 and a random supplemental input vector 420. The supplemental input vector 420 represents one or more tags, but, similarly to the latent vector 402, has random values during the training process. The generator model 144 generates a clean shape 306 (also referred to as a "fake" example because the clean shape 306 is generated by the generator model 144). The discriminator model 146 performs a classification on the generated clean shape 306.

During the discriminator training phase 400, the training process specifies which of the discriminators inputs is real and which is fake, e.g., by associating a tag value of "1" with the target shape 308 and associating a value of "0" with the generated clean shape 306. Thus, the discriminator training phase 400 trains the discriminator model 146 to classify its input as real or fake. During the discriminator training phase 400, the discriminator model 146A performs a classification based on the shape generated by the generator model 144. This classification can be further based on the same supplemental input vector 420 that is provided as input to the generator. The discriminator also performs a classification based on the target shape 308 example retrieved from the training data. This classification can be further based on a target supplemental input vector associated with the target shape 308 example and retrieved from the training data. The training process does not update the generator's weights during the discriminator training phase, so that the generator is trained at a similar rate to the discriminator.

After each occurrence of the discriminator phase, the training process performs the generator training phase, which is described herein with respect to FIG. 5.

FIG. 5 is a more detailed view of how the generator model 144 of FIG. 3 is trained, according to various embodiments. A generator training phase 500 trains the generator using a generator loss function, which determines an amount of generator loss based on a sum of a classification of the generated example and an amount of heuristic loss. The classification of the generated example can be a probability, determined by the discriminator, that the generated example is a "real" example (e.g., a target shape 308, as opposed to a generated example). The classification of the generated example is referred to herein as an "adversarial loss." The heuristic loss can be determined by a heuristic loss function based on a difference between a property value (e.g., height) of a generated clean shape and a heuristic constraint value (e.g., an average height of people who are represented by body heuristic values). The generator training phase 500 updates parameters of the generator model 144 (e.g., neural network weights) by performing backpropagation (update generator model 512) based on the generator loss.

After each occurrence of the discriminator phase 400, the training process performs the generator training phase 500, which is described herein with respect to FIG. 5. In the generator training phase 500, the training process provides random input 300 to the generator model 144 as input, as described above for the discriminator training phase 400. The generator model 144 generates a clean shape ("fake" example) 306 based on the random input and further based on the same supplemental input vector 420 that was provided as input to the generator model 144. The discriminator model 146 determines a clean shape classification 310 of clean shape 306.

A generator loss function 506 computes an adversarial loss 508 based on the clean shape classification 310. The generator loss function 506 also computes a heuristic loss 510 and combines (e.g., adds) the adversarial loss 508 and the heuristic loss 510 to generate an amount of generator loss. The heuristic loss 510 is calculated by a body heuristic loss function 504 based on one or more characteristics of the generated clean shape ("fake" example) 306 and one or more constraint values specified by one or more heuristic constraints 314. The heuristic constraints 314 can be retrieved from a database of anatomical relationships, such as the "1988 Anthropometric Survey of US Army Personnel" report database. This database includes tables of statistically meaningful relationships between anthropometric features and their regression coefficients. These relationships can be added as part of the training to bound the space of possible solutions of the generator model 144.

The body heuristic loss function 504 can determine a difference between a particular characteristic of the generated clean shape 306 and a corresponding constraint value specified in heuristic constraints 314. The corresponding value can be an average value of the particular characteristic, for example. For example, the heuristic constraint can indicate that the average height of U.S. Army personnel is 1.75 meters with a standard deviation of 0.06 meters. This can be incorporated into the generator loss function 506 by adding a term to the generator loss function 506 that penalizes deviations from the average height. This term can be, for example:

$$\text{height\_loss} = (\text{generated\_height} - \text{average\_height})^2 / (2 * \text{standard\_deviation}^2)$$

where generated_height is the height of the generated clean torso, average_height is the average height from the database of anatomical relationships (1.75 meters), and standard_deviation is the standard deviation, which is also from the database (0.06 meters).

By adding this term to the generator loss, the GAN network can be trained to generate torsos with heights close to the average height from the database of anatomical relationships. Using this term causes the GAN to generate clean shapes 306 having torsos that are representative of the size and shape of the U.S. Army population from the database.

As another example heuristic constraint, the database of anatomical relationships can show that the average waist circumference of U.S. Army personnel is 0.9 meters with a standard deviation of 0.05 meters. This can be incorporated into the generator loss function 506 by adding a term that penalizes deviations from the average waist circumference. This term can be defined as:

$$\text{waist\_loss} = (\text{generated\_waist} - \text{average\_waist})^2 / (2 * \text{standard\_deviation}^2)$$

wherein generated_waist is the waist circumference of the generated clean torso, average_waist is the average waist circumference from the database of anatomical relationships (0.9 meters), and standard_deviation is the standard deviation from the database (0.05 meters).

The training process can incorporate the heuristic constraints into the generator loss by adding the heuristic loss 510 to the adversarial loss 508 as follows:

$$\text{adversarial\_loss} = -\text{discriminator}(\text{generated\_torso}).\text{log\_prob}$$

$$\text{generator\_loss} = \text{height\_loss} + \text{waist\_loss} + \text{adversarial\_loss}$$

where "discriminator" represents the discriminator model 146, generated_torso represents the clean shape 306, and "log_prob" calculates the logarithm of a probability.

During the generator training phase, the training process does not specify which of the discriminator's inputs is real and which is fake. Further, the training process does not update the discriminator's weights during the generator training phase, so that the discriminator is trained at a similar rate to the generator.

FIG. 6 is a block diagram of the inference module 136 of FIG. 1, according to various embodiments. The inference module 136 executes a trained generator model 144 by receiving generator input 600. The inference module 136 can receive the generator input 600 from other system components such as applications. The inference module 136 provides the generator input 600 to the generator model 144. The generator input 600 can include a supplemental input vector 604 ("tags") that specify body-related characteristics of the clean shape 306 to be generated. The supplemental input vector 604 can include specific values or ranges for body characteristics such as body mass index, shoulder circumference, chest circumference, and so on. The generator model 144 generates clean shapes 606 based on the generator input 600. The clean shapes 606 include 3D objects that resemble target shapes 308 used in the model training process that conform to the heuristic constraints 314 that were used in the model training process. Additionally, if a supplemental input vector 604 was specified, then the generator model 144 generates clean shapes 606 having the characteristics specified by the supplemental input vector 604. For example, if a supplemental input vector 604 specifies a tag that represents a body height and a value of 5 feet, 7 inches, then the inference module generates clean shapes 606 resembling target shapes 308 that were associated with a target supplemental input vector 408 having the value 5 feet, 7 inches in training data 312 when the generator model 144 was trained. The inference module 136 then provides the clean shapes 606 as output, e.g., to other system components such as applications.

Figure 7:
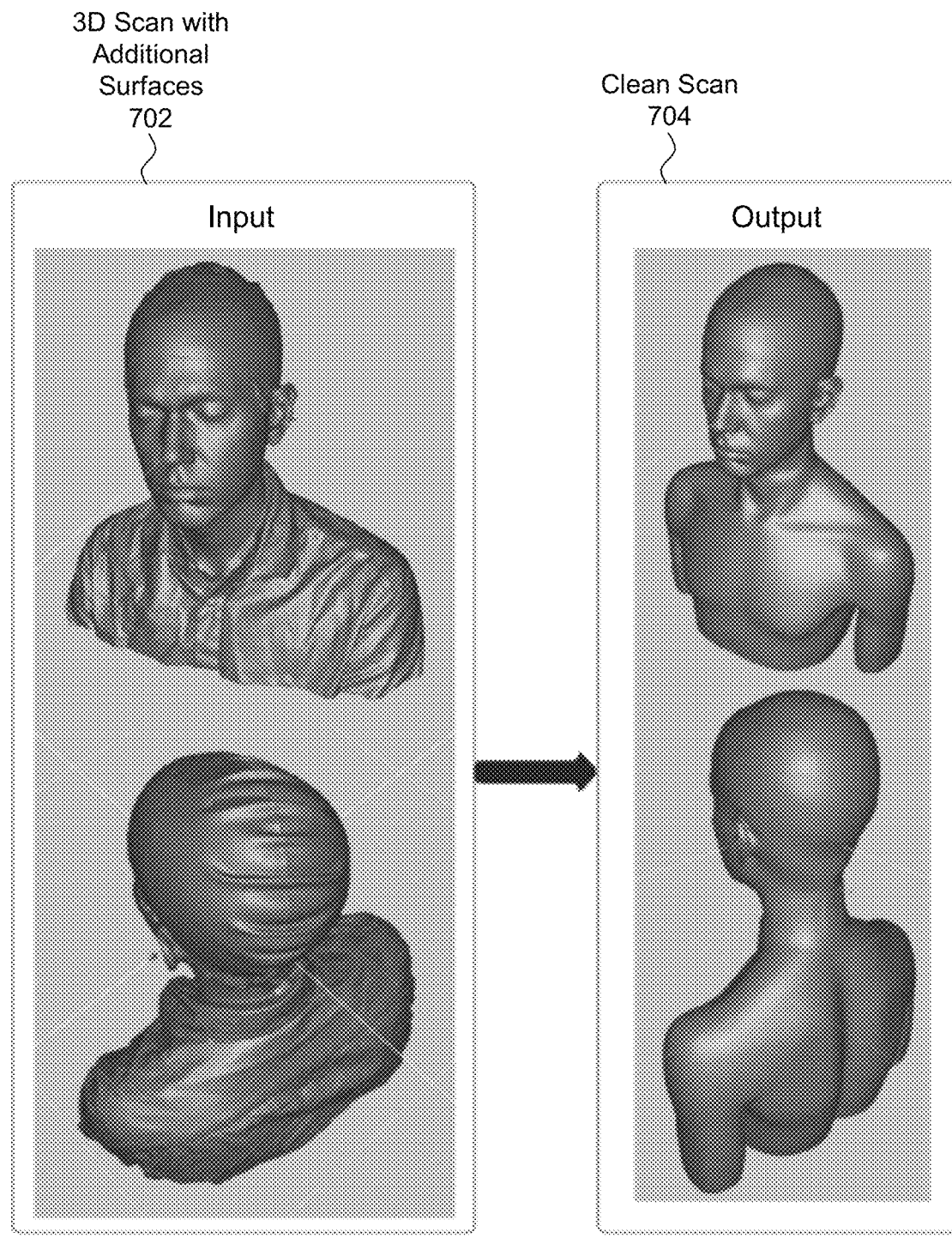
FIG. 7 illustrates how 3D scans of a human torso are processed by the computing system of FIG. 1, according to various embodiments.

FIG. 7 illustrates how 3D scans 702 of a human torso are processed by the computing system of FIG. 1, according to various embodiments. Two 3D scans 702 depicting a human head and torso from different respective viewpoints are shown. The 3D scans 702 depict additional surfaces that are not integral parts of the body structure. The additional surfaces include a hat having a partially wrinkled surface, and a shirt having a collar and a wrinkled surface. Example clean scans 704 generated by the generator model 144 depict a human head and torso from the same viewpoints as the 3D scan 702, but do not have the additional surfaces (e.g., wrinkled clothing and shirt collar) of the 3D scans 702. Thus, the clean scans 704 are suitable for use in synthesizing HRTFs.

Figure 8:
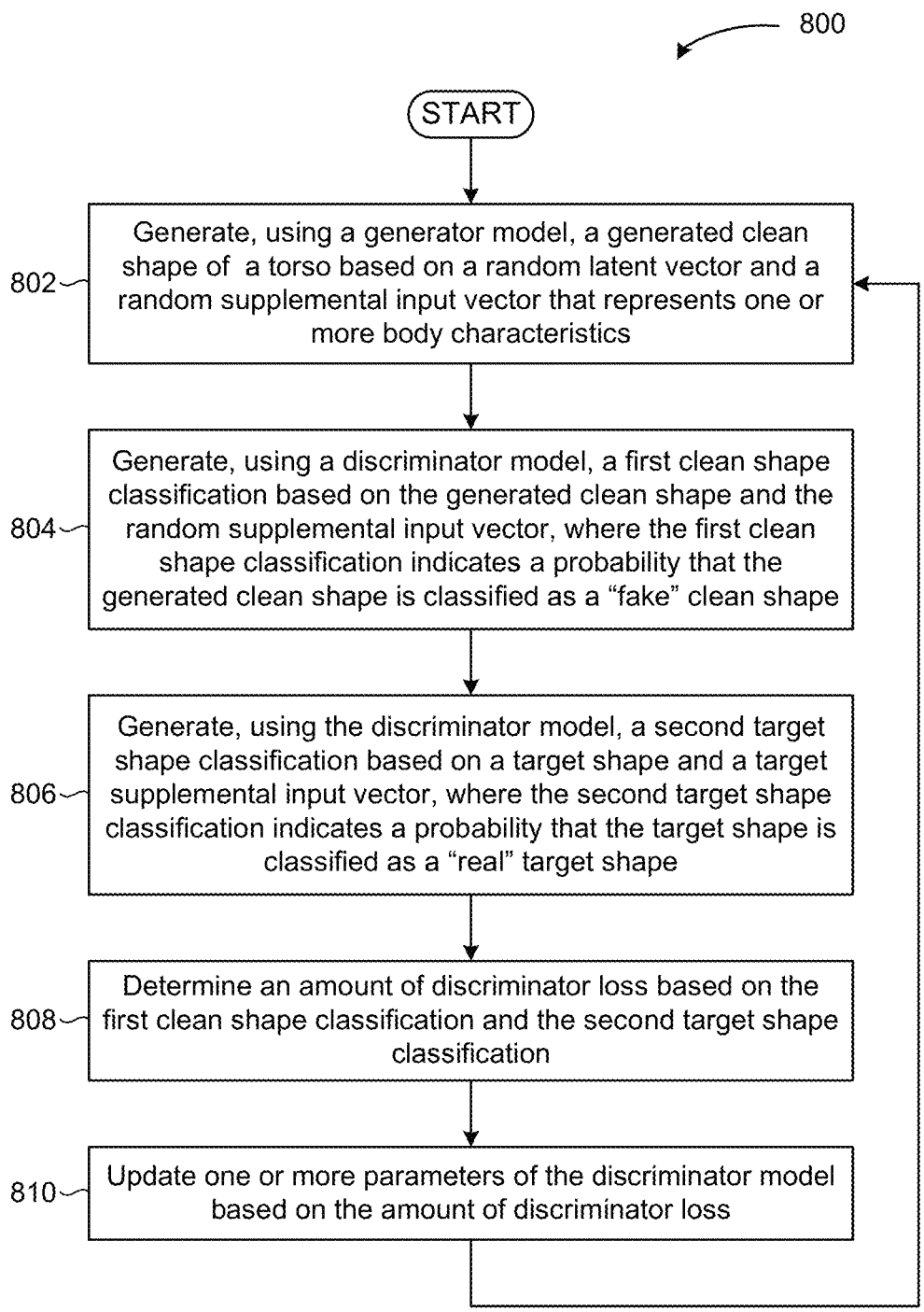
FIG. 8 is a flow diagram of method steps for training the discriminator model of FIG. 4 using 3D scans of human torsos, according to various embodiments.

FIG. 8 is a flow diagram of method steps for training the discriminator model 146 of FIG. 4 using 3D scans of human torsos, according to various embodiments. Although the method steps are described in conjunction with the systems of FIGS. 1-7, persons skilled in the art will understand that any system configured to perform the method steps, in any order, is within the scope of the present disclosure.

As shown, a method 800 begins at step 802, where a computing device 100 generates, using the generator model 144, a generated clean shape 306 of a torso based on a random latent vector 402 and a random supplemental input vector 420 that represents one or more body characteristics. In the discriminator training phase 400, the training process provides random input 300 to the generator model 144 as input. The random input 300 includes a random latent vector 402 and a random supplemental input vector 420. The supplemental input vector 420 represents one or more tags, but, similarly to the latent vector 402, has random values during the training process. The generator model 144 generates a clean shape 306 (also referred to as a "fake" example because the clean shape 306 is generated by the generator model 144).

At step 804, computing device 100 generates, using the discriminator model 146, a first clean shape classification 310 based on the generated clean shape 306 of the torso and the random supplemental input vector 420, where the first clean shape classification 310 indicates a probability that the generated clean shape 306 of the torso is classified as a "fake" torso example generated by the generator model 144. The discriminator model 146 receives a generated clean shape 306 and an optional supplemental input vector 420 as input, and classifies received shape as being either "real" (e.g., from the training data 312) or "fake" (e.g., generated by the generator model 144). The discriminator model 146 generates a clean shape classification 310 as a value between 0 and 1.0, where 1.0 indicates that the clean shape 306 is classified as fake, 0 indicates that the clean shape 306 is classified as real, and a value between 0 and 1 indicates a probability that the clean shape 306 is fake.

At step 806, computing device 100 generates, using the discriminator model 146, a second target shape classification 404 based on a target shape 308 of a torso example and a target supplemental input vector 302, where the second target shape classification 404 indicates a probability that the target shape 308 of the torso example is classified as a "real" torso example from a set of target shapes 308 of torso examples. The discriminator model 146 receives a target shape 308 and a target supplemental input vector 408 as input, and classifies the received shape as being either "real" (e.g., from the training data 312) or "fake" (e.g., generated by the generator model 144). The discriminator model 146 generates a target shape classification 404 as a value between 0 and 1.0, where 1.0 indicates that the target shape 308 is classified as real, 0 indicates that the target shape 308 is classified as fake, and a value between 0 and 1 indicates a probability that the target shape is real. Although particular probability values are described as corresponding to real and fake classification in the examples described herein, other probability values may correspond to the real and fake classifications in other examples.

At step 808 computing device 100 determines an amount determined by a discriminator loss function 410 based on the first clean shape classification 310 and the second target shape classification 404. The discriminator training phase 400 trains the discriminator using a discriminator loss function 410, which determines an amount of discriminator loss based on a sum of the two classifications 310, 404 output by the discriminator model. The discriminator loss function 410 computes a discriminator loss based on a real loss 414 and a fake loss 412. The discriminator loss is a measure of how well the discriminator model 146 is able to distinguish between real and generated samples. At step 810, computing device 100 updates one or more parameters of the discriminator model 146 (e.g., neural network weights) by performing backpropagation (update discriminator model 416) based on the amount determined by the discriminator loss function 410.

The method 800 returns to step 802 to iteratively perform steps 802-810 until the discriminator model 146 can regularly and reliably detect and distinguish between fake generated clean shapes 306 and real target shapes 308. Computing device 100 alternates between the discriminator training phase 400 and the generator training phase 500 until a threshold condition is met, such as the discriminator model 146 being unable to determine which of its inputs is real and which of its inputs is fake.

Figure 9:
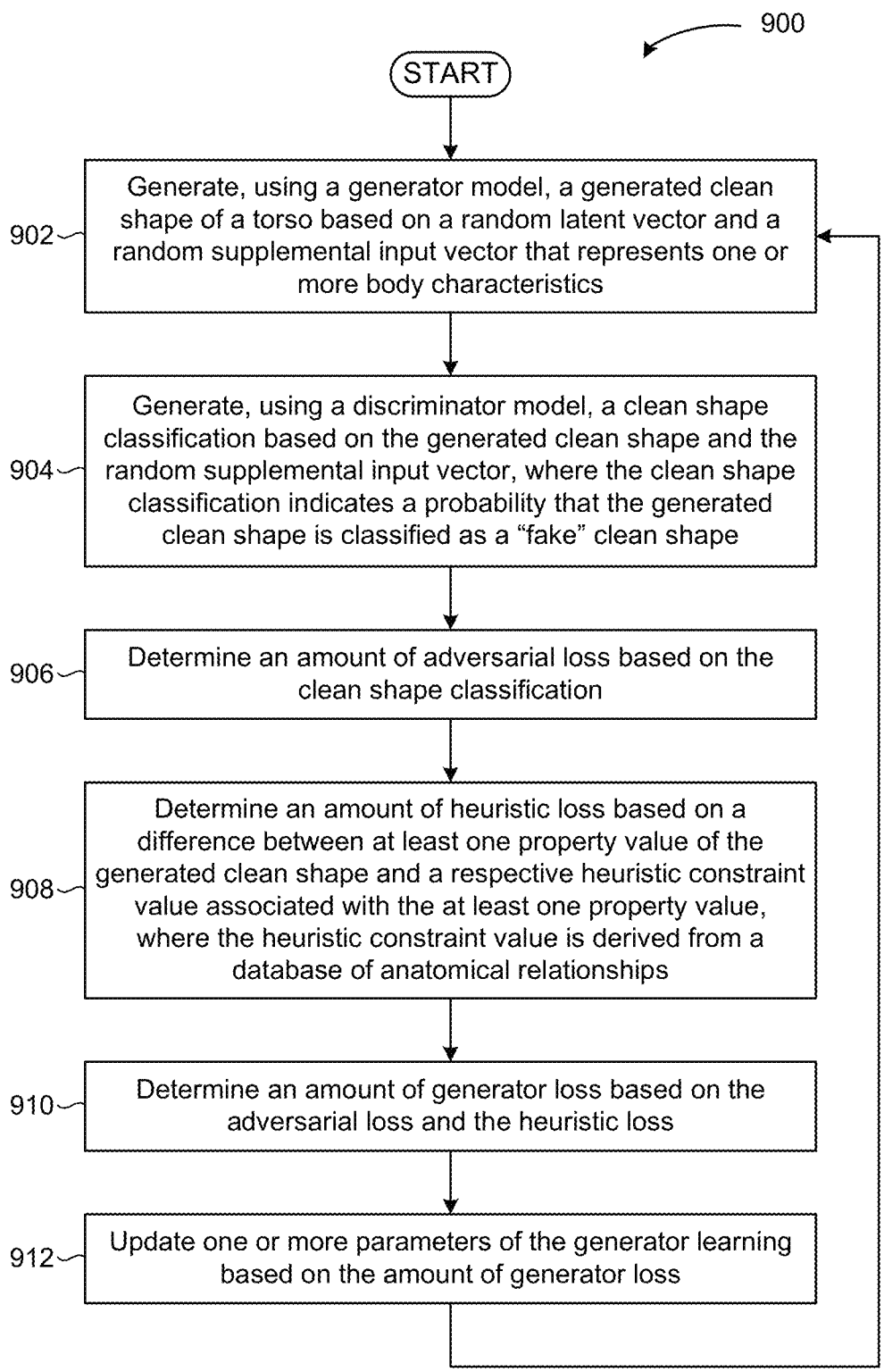
FIG. 9 is a flow diagram of method steps for training the generator model of FIG. 5 using 3D scans of human torsos, according to various embodiments.

FIG. 9 is a flow diagram of method steps for training the generator model 144 of FIG. 5 using 3D scans of human torsos, according to various embodiments. Although the method steps are described in conjunction with the systems of FIGS. 1-7, persons skilled in the art will understand that any system configured to perform the method steps, in any order, is within the scope of the present disclosure.

As shown, a method 900 begins at step 902, where a computing device 100 generates, using the generator model 144, a generated clean shape 306 of a torso based on a random latent vector 402 and a random supplemental input vector 420 that represents one or more body characteristics.

In the generator training phase 500, the training process provides random input 300 to the generator model 144 as input. The random input 300 includes a random latent vector 402 and a random supplemental input vector 420. The supplemental input vector 420 represents one or more tags, but, similarly to the latent vector 402, has random values during the training process. The generator model 144 generates a clean shape 306.

At step 904, computing device 100 generates, using the discriminator model 146, a clean shape classification 310 based on the generated clean shape 306 of the torso and the random supplemental input vector 420, where the clean shape classification 310 indicates a probability that the generated clean shape 306 of the torso is classified as a "fake" torso example generated by the generator model 144. The discriminator model 146 receives a generated clean shape 306 and an optional supplemental input vector 420 as input, and classifies received shape as being either "real" (e.g., from the training data 312) or "fake" (e.g., generated by the generator model 144). The discriminator model 146 generates a clean shape classification 310 as a value between 0 and 1.0, where 1.0 indicates that the clean shape 306 is classified as fake, 0 indicates that the clean shape 306 is classified as real, and a value between 0 and 1 indicates a probability that the clean shape 306 is fake.

At step 906, computing device 100 determines an amount of adversarial loss 508 based on the clean shape classification 310. The classification of the generated example can be a probability, determined by the discriminator, that the generated example is a "real" example (e.g., a target shape 308, as opposed to a generated example). The classification of the generated example is referred to as an "adversarial loss."

At step 908, computing device 100 determines an amount of heuristic loss 510 based on a difference between at least one property value of the generated clean shape 306 of the torso and a respective heuristic constraint 314 value associated with the at least one property value, where the heuristic constraint 314 value is derived from a database of anatomical relationships. The heuristic loss can be determined by a heuristic loss function based on a difference between a property value (e.g., height) of a generated clean shape and a heuristic constraint value (e.g., an average height of people who are represented by body heuristic values). The heuristic loss 510 is calculated by a body heuristic loss function 504 based on one or more characteristics of the generated clean shape ("fake" example) 306 and one or more constraint values specified by one or more heuristic constraints 314. The heuristic constraints 314 can be retrieved from a database of anatomical relationships. This database includes tables of statistically meaningful relationships between anthropometric features and their regression coefficients. These relationships can be added as part of the training to bound the space of possible solutions of the generator model 144, At step 910, computing device 100 determines an amount determined by a generator loss function 506 based on the adversarial loss 508 and the heuristic loss 510. A generator loss function 506 computes an adversarial loss 508 based on the clean shape classification 310. The generator loss function 506 also computes a heuristic loss 510 and combines (e.g., adds) the adversarial loss 508 and the heuristic loss 510 to generate an amount of generator loss. At step 912, computing device 100 updates one or more parameters of the generator model 144 (e.g., neural network weights) by performing backpropagation (update generator model 512) based on the amount determined by the generator loss function 506.

The method 900 returns to step 902 to iteratively perform steps 902-912 until the generator model 144 can regularly and reliably generate fake generated clean shapes 306 that the discriminator model 146 cannot detect and distinguish from real target shapes 308. Computing device 100 alternates between the discriminator training phase 400 and the generator training phase 500 until a threshold condition is met, such as the discriminator model 146 being unable to determine which of its inputs is real and which of its inputs is fake. For example, if the discriminator model 146 generates a clean shape classification 310 representing a probability of 0.5, then the training process stops because the discriminator model 146 is unable to distinguish between a target shape 308 and a clean shape 306 generated by the generator.

Figure 10:
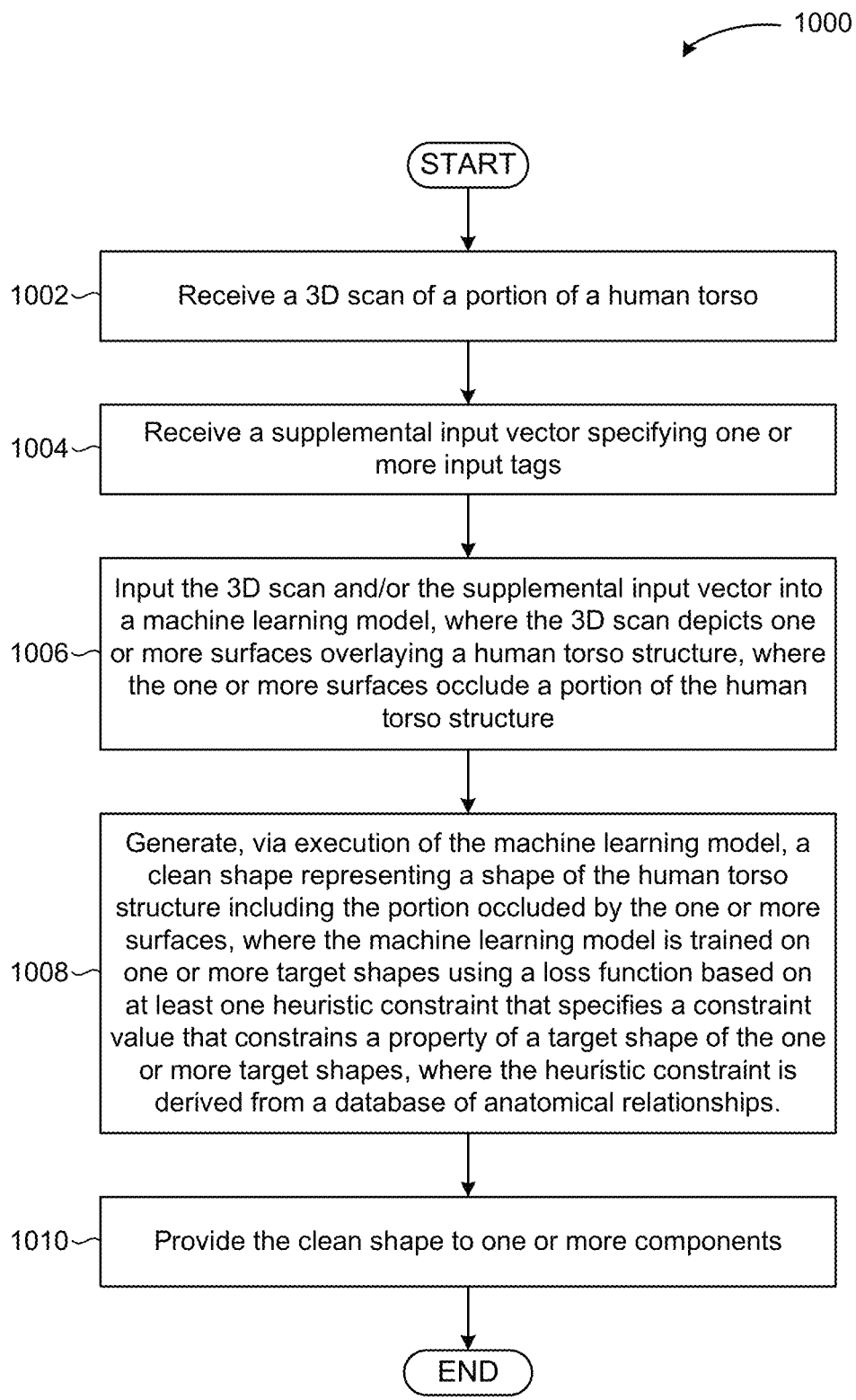
FIG. 10 is a flow diagram of method steps for using the inference model of FIG. 6 to process inference input in the form of 3D scans of human torsos, according to various embodiments.

FIG. 10 is a flow diagram of method steps for using the inference module 136 of FIG. 6 to process inference input in the form of 3D scans of human torsos, according to various embodiments. Although the method steps are described in conjunction with the systems of FIGS. 1-7, persons skilled in the art will understand that any system configured to perform the method steps, in any order, is within the scope of the present disclosure.

As shown, a method 1000 begins at step 1002, where a computing device 100 receives a 3D scan 602 of a portion of a human torso. The 3D scan 602 is obtained using a device that captures high resolution 3D models of a human subject. The device can be, a CT imager, a lidar scanner, a photogrammetry device, a camera device, and/or the like. In some examples, the skin depth of the subject is visible in the scanned 3D imagery.

At step 1004, computing device 100 receives a supplemental input vector 604 specifying one or more input tags. The supplemental input vector 604 can include tags that specify body-related characteristics of the clean shape 306 to be generated. The supplemental input vector 604 can include specific values or ranges for body characteristics such as body mass index, shoulder circumference, chest circumference, and so on.

At step 1006, computing device 100 inputs the 3D scan 602 and/or the supplemental input vector 604 into the generator model 144, where the 3D scan 602 depicts one or more surfaces overlaying a human torso structure, where the one or more surfaces occlude a portion of the human torso structure. At step 1008, computing device 100 generates, via execution of the generator model 144, a clean shape 606 representing a shape of the human torso structure including the portion occluded by the one or more surfaces. The generator model 144 generates clean shapes 606 based on the generator input 600. The clean shapes 606 include 3D objects that resemble target shapes 308 used in the model training process that conform to the heuristic constraints 314 that were used in the model training process. Additionally, if a supplemental input vector 604 was specified, then the generator model 144 generates clean shapes 606 having the characteristics specified by the supplemental input vector 604. For example, if a supplemental input vector 604 specifies a tag that represents a body height and a value of 5 feet, 7 inches, then the inference module generates clean shapes 606 resembling target shapes 308 that were associated with a target supplemental input vector 408 having the value 5 feet, 7 inches in training data 312 when the generator model 144 was trained. The inference module 136 then provides the clean shapes 606 as output, e.g., to other system components such as applications. The generator model 144 is trained on one or more target shapes 308 using a loss function based on at least one heuristic constraint 314 that specifies a constraint value that constrains a property of a target shape of the one or more target shapes 308, where the heuristic constraint 314 is derived from a database of anatomical relationships. At step 1010, computing device 100 provides the clean shape 606 to one or more components. For example, computing device 100 may provide the clean shape to an application executing on computing device 100. The application executing on computing device 100 can generate a head-related transfer function based on the clean shape 606.

In sum, a computer-based system employs a machine-learning model that predicts 3D torso shapes that approximate the physical body structure of a person given a 3D scan of the person, where the 3D scan includes additional surfaces overlaid on the physical body, such as clothing or hair. The additional surfaces change the shape of the person but do not reflect, refract, or block sound waves to the extent the physical body does. The system corrects the distorted 3D scan and generates an improved 3D model of the torso. The torso shape generated by the machine-learning model approximates the shape of the physical body without the additional surfaces and can be used for synthesis of HRTFs through acoustic simulations, or through the generation of physical 3D models of the scanned subject.

The machine-learning model is generated by training a ML/AI model with a target dataset that includes scanned 3D imagery of human torsos. The scanned 3D imagery is obtained using a device that captures high resolution 3D models of a human subject. The device can be a CT imager, a lidar scanner, a photogrammetry device, a camera device, and/or the like. In some examples, the skin depth of the subject is visible in the scanned 3D imagery. The target dataset is processed using heuristics that indicate a desired acoustic performance when synthesizing HRTFs based on the 3D models that are processed to include an anatomically correct torso. These heuristics include body volume, shape consistency, proportions, joint locations, symmetry, and/or the like. The desired acoustic performance is defined as the difference between the synthesized HRTF and the measured HRTF for each subject in the target dataset. This difference can be quantified as a difference in acoustical pressure or as a psychoacoustic performance in terms of sound quality or localization accuracy.

The target dataset is then used to generate a machine-learning model that describes the transformation applied to a new scan of a subject as captured by a computing system fitted with sensors and/or scanning devices. The scan may represent the 3D shape of the subject, including acoustically transparent object such as clothes and hair. The machine-learning model generates a "clean" shape based on the scanned shape. The clean shape is a modification of the scanned shape such that the clean shape resembles target shapes used in the model training process, and conforms to heuristic constraints that were also used in the model training process. The target shapes represent portions of a human body, such as torsos. The target shapes do not have acoustically transparent surfaces such as clothing or hair. The heuristic constraints can specify characteristics of portions of average of representative human bodies, and may be specified in a database of anatomical relationships. The clean shape is thus a modified shape that is similar to the scanned shape but does not include portions of the scanned shape that are acoustically transparent. As such, the clean shape is suitable for use in synthesizing HRTFs.

At least one technical advantage of the disclosed techniques relative to the prior art is that 3D torso models for synthesizing head-related transfer functions can be generated faster and more accurately than with prior conventional approaches. In particular, the 3D torso models generated with the disclosed techniques do not include surfaces that are not acoustically relevant for HRTF purposes, such as wrinkles on a t-shirt and/or other clothing surfaces. As a result, these 3D torso models can be used to synthesize and generate individualized HRTF without the need for manual processes to remove acoustically transparent surfaces from the 3D torso models. Further, manual processes can introduce errors, asymmetry, and inaccuracy in the resulting 3D model. By contrast, 3D torso models generated with the disclosed techniques are more accurate and consistent with the shape of the torso of the subject being scanned. As a result, synthesized HRTF data derived from these 3D torso models are likewise more accurate and suitable for the subject being scanned. These technical advantages represent one or more technological improvements over prior art approaches.

1. In some embodiments, a computer-implemented method for generating torso shapes suitable for synthesis of head-related transfer functions comprises inputting a three-dimensional (3D) scan into a machine learning model, wherein the 3D scan depicts one or more surfaces overlaying a human body structure comprising a torso of a user, wherein the one or more surfaces occlude a portion of the torso; generating, via execution of the machine learning model, a clean shape representing a shape of the torso including the portion occluded by the one or more surfaces, wherein the machine learning model is trained on one or more target shapes using a loss function based on at least one heuristic constraint that specifies a constraint value that constrains a property of a first target shape of the one or more target shapes, wherein the heuristic constraint is derived from a database of anatomical relationships; and causing the clean shape to be outputted in a computing device, wherein the clean shape is suitable for generating an accurate head-related transfer function for the user.
2. The computer-implemented method of clause 1, wherein the loss function determines a difference between the constraint value specified by the heuristic constraint and a value of the property of the first target shape.
3. The computer-implemented method of clauses 1 or 2, wherein the loss function determines a difference between the constraint value specified by the heuristic constraint and a value of the property of the first target shape.
4. The computer-implemented method of any of clauses 1-3, wherein the constraint value is an average value of the property, and the average value of the property is specified by the database of anatomical relationships.
5. The computer-implemented method of any of clauses 1-4, further comprising: receiving a supplemental input vector from a user, wherein the supplemental input vector comprises at least one tag specifying at least one anatomical property of the user; and inputting the supplemental input vector into the machine learning model, wherein the clean shape generated via execution of the machine learning model is based on the at least one anatomical property of the user.
6. The computer-implemented method of any of clauses 1-5, wherein the machine learning model is trained further based on an association between the one or more target shapes and the supplemental input vector.
7. The computer-implemented method of any of clauses 1-6, wherein the at least one anatomical property of the user comprises one or more of a body height, a torso height, a chest circumference, a waist circumference, a body mass index, a shoulder width to torso height ratio, or a shoulder width to body mass index ratio.
8. The computer-implemented method of any of clauses 1-7, further comprising generating the head-related transfer function from the clean shape.
9. The computer-implemented method of any of clauses 1-8, wherein the one or more surfaces are acoustically transparent.
10. The computer-implemented method of any of clauses 1-9, wherein the machine learning model comprises a generator model of a generative adversarial network.
11. In some embodiments, one or more non-transitory computer readable media include instructions that, when executed by one or more processors, cause the one or more processors to perform the steps of inputting a three-dimensional (3D) scan into a machine learning model, wherein the 3D scan depicts one or more surfaces overlaying a human body structure comprising a torso of a user, wherein the one or more surfaces occlude a portion of the torso; generating, via execution of the machine learning model, a clean shape representing a shape of the torso including the portion occluded by the one or more surfaces, wherein the machine learning model is trained on one or more target shapes using a loss function based on at least one heuristic constraint that specifies a constraint value that constrains a property of a first target shape of the one or more target shapes, wherein the heuristic constraint is derived from a database of anatomical relationships; and causing the clean shape to be outputted in a computing device, wherein the clean shape is suitable for generating an accurate head-related transfer function for the user.
12. The one or more non-transitory computer readable media of clause 11, wherein the loss function determines a difference between the constraint value specified by the heuristic constraint and a value of the property of the first target shape.
13. The one or more non-transitory computer readable media of clauses 11 or 12, wherein the constraint value comprises one or more of a body height, a torso height, a chest circumference, a waist circumference, a body mass index, a shoulder width to torso height ratio, or a shoulder width to body mass index ratio.
14. The one or more non-transitory computer readable media of any of clauses 11-13, wherein the constraint value is an average value of the property, and the average value of the property is specified by the database of anatomical relationships.
15. The one or more non-transitory computer readable media of any of clauses 11-14, wherein the steps further comprise: receiving a supplemental input vector from a user, wherein the supplemental input vector comprises at least one tag specifying at least one anatomical property of the user; and inputting the supplemental input vector into the machine learning model, wherein the clean shape generated via execution of the machine learning model is based on the at least one anatomical property of the user.
16. The one or more non-transitory computer readable media of any of clauses 11-15, wherein the machine learning model is trained further based on an association between the one or more target shapes and the supplemental input vector.

17. The one or more non-transitory computer readable media of any of clauses 11-16, wherein the at least one anatomical property of the user comprises one or more of a body height, a torso height, a chest circumference, a waist circumference, a body mass index, a shoulder width to torso height ratio, or a shoulder width to body mass index ratio.

18. The one or more non-transitory computer readable media of any of clauses 11-17, further comprising generating the head-related transfer function from the clean shape.

19. The one or more non-transitory computer readable media of any of clauses 11-18, wherein the one or more surfaces are acoustically transparent.

20. In some embodiments, a system comprises one or more memories storing instructions; and one or more processors that are coupled to the one or more memories and, when executing the instructions, are configured to input a three-dimensional (3D) scan into a machine learning model, wherein the 3D scan depicts one or more surfaces overlaying a human body structure comprising a torso of a user, wherein the one or more surfaces occlude a portion of the torso; generate, via execution of the machine learning model, a clean shape representing a shape of the torso including the portion occluded by the one or more surfaces, wherein the machine learning model is trained on one or more target shapes using a loss function based on at least one heuristic constraint that specifies a constraint value that constrains a property of a first target shape of the one or more target shapes, wherein the heuristic constraint is derived from a database of anatomical relationships; and cause the clean shape to be outputted in a computing device, wherein the clean shape is suitable for generating an accurate head-related transfer function for the user.

Any and all combinations of any of the claim elements recited in any of the claims and/or any elements described in this application, in any fashion, fall within the contemplated scope of the present disclosure and protection.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method, or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Aspects of the present disclosure are described above with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, enable the implementation of the functions/acts specified in the flowchart and/or block diagram block or blocks. Such processors may be, without limitation, general purpose processors, special-purpose processors, application-specific processors, or field-programmable gate arrays.

The flowchart and block diagrams in the figures illustrate the architecture, functionality, and operation of possible implementations of systems, methods, and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

While the preceding is directed to embodiments of the present disclosure, other and further embodiments of the disclosure may be devised without departing from the basic scope thereof, and the scope thereof is determined by the claims that follow.

What is claimed is:

1. A computer-implemented method for generating torso shapes suitable for synthesis of head-related transfer functions, the method comprising:
    inputting a three-dimensional (3D) scan into a machine learning model, wherein the 3D scan depicts one or more surfaces overlaying a human body structure comprising a torso of a user, wherein the one or more surfaces occlude a portion of the torso;

generating, via execution of the machine learning model, a clean shape representing a shape of the torso including the portion occluded by the one or more surfaces, wherein the machine learning model is trained on one or more target shapes using a loss function based on at least one heuristic constraint that specifies a constraint value that constrains a property of a first target shape of the one or more target shapes, wherein the heuristic constraint is derived from a database of anatomical relationships; and causing the clean shape to be outputted in a computing device, wherein the clean shape is suitable for generating an accurate head-related transfer function for the user.

2. The method of claim 1, wherein the loss function determines a difference between the constraint value specified by the heuristic constraint and a value of the property of the first target shape.

3. The method of claim 1, wherein the constraint value comprises one or more of a body height, a torso height, a chest circumference, a waist circumference, a body mass index, a shoulder width to torso height ratio, or a shoulder width to body mass index ratio.

4. The method of claim 1, wherein the constraint value is an average value of the property, and the average value of the property is specified by the database of anatomical relationships.

5. The method of claim 1, further comprising:
receiving a supplemental input vector from the user, wherein the supplemental input vector comprises at least one tag specifying at least one anatomical property of the user; and
inputting the supplemental input vector into the machine learning model,
wherein the clean shape generated via execution of the machine learning model is based on the at least one anatomical property of the user.

6. The method of claim 5, wherein the machine learning model is trained further based on an association between the one or more target shapes and the supplemental input vector.

7. The method of claim 5, wherein the at least one anatomical property of the user comprises one or more of a body height, a torso height, a chest circumference, a waist circumference, a body mass index, a shoulder width to torso height ratio, or a shoulder width to body mass index ratio.

8. The method of claim 1, further comprising generating the head-related transfer function from the clean shape.

9. The method of claim 1, wherein the one or more surfaces are acoustically transparent.

10. The method of claim 1, wherein the machine learning model comprises a generator model of a generative adversarial network.

11. One or more non-transitory computer-readable media storing program instructions that, when executed by one or more processors, cause the one or more processors to perform steps of:
inputting a three-dimensional (3D) scan into a machine learning model, wherein the 3D scan depicts one or more surfaces overlaying a human body structure comprising a torso of a user, wherein the one or more surfaces occlude a portion of the torso;
generating, via execution of the machine learning model, a clean shape representing a shape of the torso including the portion occluded by the one or more surfaces, wherein the machine learning model is trained on one or more target shapes using a loss function based on at least one heuristic constraint that specifies a constraint value that constrains a property of a first target shape of the one or more target shapes, wherein the heuristic constraint is derived from a database of anatomical relationships; and
causing the clean shape to be outputted in a computing device, wherein the clean shape is suitable for generating an accurate head-related transfer function for the user.

12. The one or more non-transitory computer-readable media of claim 11, wherein the loss function determines a difference between the constraint value specified by the heuristic constraint and a value of the property of the first target shape.

13. The one or more non-transitory computer-readable media of claim 11, wherein the constraint value comprises one or more of a body height, a torso height, a chest circumference, a waist circumference, a body mass index, a shoulder width to torso height ratio, or a shoulder width to body mass index ratio.

14. The one or more non-transitory computer-readable media of claim 11, wherein the constraint value is an average value of the property, and the average value of the property is specified by the database of anatomical relationships.

15. The one or more non-transitory computer-readable media of claim 11, wherein the steps further comprise:
receiving a supplemental input vector from the user, wherein the supplemental input vector comprises at least one tag specifying at least one anatomical property of the user; and
inputting the supplemental input vector into the machine learning model,
wherein the clean shape generated via execution of the machine learning model is based on the at least one anatomical property of the user.

16. The one or more non-transitory computer-readable media of claim 15, wherein the machine learning model is trained further based on an association between the one or more target shapes and the supplemental input vector.

17. The one or more non-transitory computer-readable media of claim 15, wherein the at least one anatomical property of the user comprises one or more of a body height, a torso height, a chest circumference, a waist circumference, a body mass index, a shoulder width to torso height ratio, or a shoulder width to body mass index ratio.

18. The one or more non-transitory computer-readable media of claim 11, further comprising generating the head-related transfer function from the clean shape.

19. The one or more non-transitory computer-readable media of claim 11, wherein the one or more surfaces are acoustically transparent.

20. A system, comprising:
one or more memories storing instructions; and
one or more processors coupled to the one or more memories that, when executing the instructions:
input a three-dimensional (3D) scan into a machine learning model, wherein the 3D scan depicts one or more surfaces overlaying a human body structure comprising a torso of a user, wherein the one or more surfaces occlude a portion of the torso;
generate, via execution of the machine learning model, a clean shape representing a shape of the torso including the portion occluded by the one or more surfaces, wherein the machine learning model is trained on one or more target shapes using a loss function based on at least one heuristic constraint that specifies a constraint value that constrains a property of a first target shape of the one or more target shapes, wherein the heuristic constraint is derived from a database of anatomical relationships; and cause the clean shape to be outputted in a computing device, wherein the clean shape is suitable for generating an accurate head-related transfer function for the user.

\* \* \* \* \*